United States Patent
Wei et al.

(10) Patent No.: US 8,394,113 B2
(45) Date of Patent: Mar. 12, 2013

(54) COILED ANCHOR DEVICE

(75) Inventors: Michael Wei, Redwood City, CA (US); Theodore C. Lamson, Pleasanton, CA (US); Joseph Catanese, III, San Leandro, CA (US)

(73) Assignee: Neotract, Inc., Pleasanton, CA (US)

( * ) Notice: Subject to any disclaimer, the term of this patent is extended or adjusted under 35 U.S.C. 154(b) by 309 days.

(21) Appl. No.: 12/852,729

(22) Filed: Aug. 9, 2010

(65) Prior Publication Data

US 2011/0040326 A1   Feb. 17, 2011

Related U.S. Application Data

(63) Continuation-in-part of application No. 12/852,243, filed on Aug. 6, 2010, now Pat. No. 8,333,776, which is a continuation-in-part of application No. 12/521,674, filed on Jul. 30, 2009, now Pat. No. 8,216,254, said application No. 12/852,243 is a continuation-in-part of application No. 11/775,162, filed on Jul. 9, 2007, and a (Continued)

(51) Int. Cl.
 *A61B 17/08* (2006.01)
(52) U.S. Cl. ..................................... 606/151
(58) Field of Classification Search .............. 606/99, 606/139, 151, 153, 232, 223, 213, 215–217, 606/155–156; 623/13.13–13.14, 17.16
 See application file for complete search history.

(56) References Cited

U.S. PATENT DOCUMENTS

| | | | |
|---|---|---|---|
| 659,422 A | 10/1900 | Shidler | |
| 780,392 A | 1/1905 | Wanamaker et al. | |
| 789,467 A | 5/1905 | West | |
| 2,579,192 A | 12/1951 | Kohl | |
| 2,646,298 A | 7/1953 | Leary | |
| 2,697,624 A | 12/1954 | Thomas | |
| 2,734,299 A | 2/1956 | Masson | |
| 2,825,592 A | 3/1958 | Semple | |
| 3,326,586 A | 6/1967 | Frost et al. | |
| 3,470,834 A | 10/1969 | Bone | |
| 3,521,918 A | 7/1970 | Hammond | |
| 3,713,680 A | 1/1973 | Pagano | |
| 3,716,058 A | 2/1973 | Tanner, Jr. | |
| 3,756,638 A | 9/1973 | Stockberger | |
| 3,873,140 A | 3/1975 | Bloch | |
| 3,875,648 A | 4/1975 | Bone | |
| 3,931,667 A | 1/1976 | Merser et al. | |

(Continued)

FOREIGN PATENT DOCUMENTS

DE   10159470   6/2003
EP   0246836   12/1991

(Continued)

OTHER PUBLICATIONS

Sharp, Howard T., M.D., et al., "Instruments and Methods—the 4-S Modification of the Roeder Knot: How to Tie It", Obstetrics & Gynecology, p. 1004-1006, vol. 90, No. 6, Dec. 1997.

(Continued)

*Primary Examiner* — Corrine M McDermott
*Assistant Examiner* — Gregory Anderson
(74) *Attorney, Agent, or Firm* — Steptoe & Johnson LLP

(57) ABSTRACT

A coiled anchor that secures to a connector as part of an anchor assembly is disclosed. The coiled anchor includes windings which capture and deform the connector between the windings and prevent the connector from disengaging from the coiled anchor once engaged.

29 Claims, 11 Drawing Sheets

Related U.S. Application Data continuation-in-part of application No. 11/671,914, filed on Feb. 6, 2007, now Pat. No. 8,157,815, and a continuation-in-part of application No. 11/492,690, filed on Jul. 24, 2006, now Pat. No. 7,896,891, and a continuation-in-part of application No. 11/833,660, filed on Aug. 3, 2007, which is a continuation of application No. 11/318,246, filed on Dec. 22, 2005, now Pat. No. 7,645,286, said application No. 12/852,243 is a continuation-in-part of application No. 11/838,036, filed on Aug. 13, 2007, now Pat. No. 7,914,542, which is a continuation of application No. 11/134,870, filed on May 20, 2005, now Pat. No. 7,758,594.

(60) Provisional application No. 61/084,937, filed on Jul. 30, 2008.

(56) References Cited

U.S. PATENT DOCUMENTS

| | | | |
|---|---|---|---|
| 3,976,079 | A | 8/1976 | Samuels et al. |
| 4,006,747 | A | 2/1977 | Kronenthal et al. |
| 4,210,148 | A | 7/1980 | Stivala |
| 4,235,238 | A | 11/1980 | Ogiu et al. |
| 4,291,698 | A | 9/1981 | Fuchs et al. |
| 4,409,974 | A | 10/1983 | Freedland |
| 4,493,323 | A | 1/1985 | Albright et al. |
| 4,513,746 | A | 4/1985 | Aranyi et al. |
| 4,621,640 | A | 11/1986 | Mulhollan et al. |
| 4,657,461 | A | 4/1987 | Smith |
| 4,669,473 | A | 6/1987 | Richards et al. |
| 4,705,040 | A | 11/1987 | Mueller et al. |
| 4,714,281 | A | 12/1987 | Peck |
| 4,738,255 | A | 4/1988 | Goble et al. |
| 4,741,330 | A | 5/1988 | Hayhurst |
| 4,744,364 | A | 5/1988 | Kensey |
| 4,750,492 | A | 6/1988 | Jacobs |
| 4,762,128 | A | 8/1988 | Rosenbluth |
| 4,823,794 | A | 4/1989 | Pierce |
| 4,899,743 | A | 2/1990 | Nicholson et al. |
| 4,926,860 | A | 5/1990 | Stice et al. |
| 4,946,468 | A | 8/1990 | Li |
| 4,955,913 | A | 9/1990 | Robinson |
| 4,968,315 | A | 11/1990 | Gatturna |
| 5,002,550 | A | 3/1991 | Li |
| 5,041,129 | A | 8/1991 | Hayhurst et al. |
| 5,046,513 | A | 9/1991 | Gatturna et al. |
| 5,053,046 | A | 10/1991 | Janese |
| 5,100,421 | A | 3/1992 | Christoudias |
| 5,123,914 | A | 6/1992 | Cope |
| 5,129,912 | A | 7/1992 | Noda et al. |
| 5,192,303 | A | 3/1993 | Gatturna et al. |
| 5,203,787 | A | 4/1993 | Noblitt et al. |
| 5,217,470 | A | 6/1993 | Weston |
| 5,217,486 | A | 6/1993 | Rice et al. |
| 5,234,454 | A | 8/1993 | Bangs |
| 5,236,445 | A | 8/1993 | Hayhurst et al. |
| 5,258,015 | A | 11/1993 | Li et al. |
| 5,269,809 | A | 12/1993 | Hayhurst et al. |
| 5,330,488 | A | 7/1994 | Goldrath |
| 5,334,200 | A | 8/1994 | Johnson |
| 5,336,240 | A | 8/1994 | Metzler et al. |
| 5,354,271 | A | 10/1994 | Voda |
| 5,358,511 | A | 10/1994 | Gatturna et al. |
| 5,364,408 | A | 11/1994 | Gordon |
| 5,366,490 | A | 11/1994 | Edwards et al. |
| 5,368,599 | A | 11/1994 | Hirsch et al. |
| 5,370,646 | A | 12/1994 | Reese et al. |
| 5,380,334 | A | 1/1995 | Torrie et al. |
| 5,391,182 | A | 2/1995 | Chin |
| 5,403,348 | A | 4/1995 | Bonutti |
| 5,405,352 | A | 4/1995 | Weston |
| 5,411,520 | A | 5/1995 | Nash et al. |
| 5,417,691 | A | 5/1995 | Hayhurst |
| 5,435,805 | A | 7/1995 | Edwards et al. |
| 5,470,337 | A | 11/1995 | Moss |
| 5,472,446 | A | 12/1995 | De la Torre |
| 5,480,406 | A | 1/1996 | Nolan et al. |
| 5,501,690 | A | 3/1996 | Measamer et al. |
| 5,507,754 | A | 4/1996 | Green et al. |
| 5,522,846 | A | 6/1996 | Bonutti |
| 5,531,763 | A | 7/1996 | Mastri et al. |
| 5,536,240 | A | 7/1996 | Edwards et al. |
| 5,540,704 | A | 7/1996 | Gordon et al. |
| 5,545,171 | A | 8/1996 | Sharkey et al. |
| 5,545,178 | A | 8/1996 | Kensey et al. |
| 5,550,172 | A | 8/1996 | Regula et al. |
| 5,554,162 | A | 9/1996 | DeLange |
| 5,554,171 | A | 9/1996 | Gatturna et al. |
| 5,562,689 | A | 10/1996 | Green et al. |
| 5,569,305 | A | 10/1996 | Bonutti |
| 5,571,104 | A | 11/1996 | Li |
| 5,573,540 | A | 11/1996 | Yoon |
| 5,578,044 | A | 11/1996 | Gordon et al. |
| 5,591,177 | A | 1/1997 | Lehrer |
| 5,593,421 | A | 1/1997 | Bauer |
| 5,611,515 | A | 3/1997 | Benderev et al. |
| 5,626,614 | A | 5/1997 | Hart |
| 5,630,824 | A | 5/1997 | Hart |
| 5,647,836 | A | 7/1997 | Blake, III et al. |
| 5,665,109 | A | 9/1997 | Yoon |
| 5,667,486 | A | 9/1997 | Mikulich et al. |
| 5,669,917 | A | 9/1997 | Sauer et al. |
| 5,690,649 | A | 11/1997 | Li |
| 5,690,677 | A | 11/1997 | Schmieding et al. |
| 5,697,950 | A | 12/1997 | Fucci et al. |
| 5,707,394 | A | 1/1998 | Miller et al. |
| 5,716,368 | A | 2/1998 | De la Torre |
| 5,718,717 | A | 2/1998 | Bonutti |
| 5,725,556 | A | 3/1998 | Moser et al. |
| 5,725,557 | A | 3/1998 | Gatturna et al. |
| 5,733,306 | A | 3/1998 | Bonutti |
| 5,741,276 | A | 4/1998 | Poloyko et al. |
| 5,746,753 | A | 5/1998 | Sullivan et al. |
| 5,749,846 | A | 5/1998 | Edwards et al. |
| 5,752,963 | A | 5/1998 | Allard et al. |
| 5,782,862 | A | 7/1998 | Bonutti |
| 5,782,864 | A | 7/1998 | Lizardi |
| 5,800,445 | A | 9/1998 | Ratcliff et al. |
| 5,807,403 | A | 9/1998 | Beyar et al. |
| 5,810,848 | A | 9/1998 | Hayhurst |
| 5,814,072 | A | 9/1998 | Bonutti |
| 5,830,221 | A | 11/1998 | Stein |
| 5,845,645 | A | 12/1998 | Bonutti |
| 5,846,254 | A | 12/1998 | Schulze et al. |
| 5,861,002 | A | 1/1999 | Desai |
| 5,868,762 | A | 2/1999 | Cragg et al. |
| 5,873,891 | A | 2/1999 | Sohn |
| 5,897,574 | A | 4/1999 | Bonutti |
| 5,899,911 | A | 5/1999 | Carter |
| 5,899,921 | A | 5/1999 | Caspari et al. |
| 5,904,696 | A | 5/1999 | Rosenman |
| 5,908,428 | A | 6/1999 | Scirica et al. |
| 5,919,198 | A | 7/1999 | Graves, Jr. et al. |
| 5,919,202 | A | 7/1999 | Yoon |
| 5,921,986 | A | 7/1999 | Bonutti |
| 5,928,252 | A | 7/1999 | Steadman et al. |
| 5,931,844 | A | 8/1999 | Thompson et al. |
| 5,944,739 | A | 8/1999 | Zlock et al. |
| 5,948,001 | A | 9/1999 | Larsen |
| 5,948,002 | A | 9/1999 | Bonutti |
| 5,954,057 | A | 9/1999 | Li |
| 5,954,747 | A | 9/1999 | Clark |
| 5,964,732 | A | 10/1999 | Willard |
| 5,971,447 | A | 10/1999 | Steck, III |
| 6,010,514 | A | 1/2000 | Burney et al. |
| 6,011,525 | A | 1/2000 | Piole |
| 6,030,393 | A | 2/2000 | Corlew |
| 6,033,430 | A | 3/2000 | Bonutti |
| 6,036,701 | A | 3/2000 | Rosenman |
| 6,048,351 | A | 4/2000 | Gordon et al. |
| 6,053,908 | A | 4/2000 | Crainich et al. |
| 6,056,722 | A | 5/2000 | Jayaraman |
| 6,056,772 | A | 5/2000 | Bonutti |

| | | | | | | |
|---|---|---|---|---|---|---|
| 6,068,648 | A | 5/2000 | Cole et al. | 6,835,200 B2 | 12/2004 | Laufer et al. |
| 6,080,167 | A | 6/2000 | Lyell | 6,905,475 B2 | 6/2005 | Hauschild et al. |
| 6,086,608 | A | 7/2000 | Ek et al. | 6,908,473 B2 | 6/2005 | Skiba et al. |
| 6,110,183 | A | 8/2000 | Cope | 6,926,732 B2 | 8/2005 | Derus et al. |
| 6,117,160 | A | 9/2000 | Bonutti | 6,951,565 B2 | 10/2005 | Keane et al. |
| 6,117,161 | A | 9/2000 | Li et al. | 6,986,775 B2 | 1/2006 | Morales et al. |
| 6,120,539 | A | 9/2000 | Eldridge et al. | 6,986,784 B1 * | 1/2006 | Weiser et al. ............... 623/1.1 |
| 6,139,555 | A | 10/2000 | Hart et al. | 6,991,596 B2 | 1/2006 | Whalen et al. |
| RE36,974 | E | 11/2000 | Bonutti | 6,991,647 B2 | 1/2006 | Jadhav |
| 6,143,006 | A | 11/2000 | Chan | 6,997,940 B2 | 2/2006 | Bonutti |
| 6,159,234 | A | 12/2000 | Bonutti et al. | 7,001,327 B2 | 2/2006 | Whalen et al. |
| 6,200,329 | B1 | 3/2001 | Fung et al. | 7,011,688 B2 | 3/2006 | Gryska et al. |
| 6,206,895 | B1 | 3/2001 | Levinson | 7,015,253 B2 | 3/2006 | Escandon et al. |
| 6,228,096 | B1 | 5/2001 | Marchand | 7,048,698 B2 | 5/2006 | Whalen et al. |
| 6,258,124 | B1 | 7/2001 | Darois et al. | 7,048,747 B2 | 5/2006 | Arcia et al. |
| 6,261,302 | B1 | 7/2001 | Voegele et al. | 7,060,077 B2 | 6/2006 | Gordon et al. |
| 6,270,530 | B1 | 8/2001 | Eldridge et al. | 7,081,126 B2 | 7/2006 | McDevitt et al. |
| 6,280,460 | B1 | 8/2001 | Bolduc et al. | 7,083,638 B2 | 8/2006 | Foerster |
| 6,290,711 | B1 | 9/2001 | Caspari et al. | 7,087,073 B2 | 8/2006 | Bonutti |
| 6,312,448 | B1 | 11/2001 | Bonutti | 7,089,064 B2 | 8/2006 | Manker et al. |
| 6,319,263 | B1 | 11/2001 | Levinson | 7,090,690 B2 | 8/2006 | Foerster et al. |
| 6,322,112 | B1 | 11/2001 | Duncan | 7,093,601 B2 | 8/2006 | Manker et al. |
| 6,332,889 | B1 | 12/2001 | Sancoff et al. | 7,105,004 B2 | 9/2006 | Dicesare et al. |
| 6,398,795 | B1 | 6/2002 | McAlister et al. | 7,108,655 B2 | 9/2006 | Whalen et al. |
| 6,425,900 | B1 | 7/2002 | Knodel et al. | 7,141,038 B2 | 11/2006 | Whalen et al. |
| 6,428,562 | B2 | 8/2002 | Bonutti | 7,153,314 B2 | 12/2006 | Laufer et al. |
| 6,436,107 | B1 | 8/2002 | Wang et al. | 7,179,225 B2 | 2/2007 | Shluzas |
| 6,461,355 | B2 | 10/2002 | Svejkovsky et al. | 7,226,558 B2 | 6/2007 | Nieman et al. |
| 6,482,235 | B1 | 11/2002 | Lambrecht et al. | 7,232,448 B2 | 6/2007 | Battles et al. |
| 6,488,691 | B1 | 12/2002 | Carroll et al. | 7,288,063 B2 | 10/2007 | Petros et al. |
| 6,491,707 | B2 | 12/2002 | Makower et al. | 7,303,108 B2 | 12/2007 | Shelton, IV |
| 6,494,888 | B1 | 12/2002 | Laufer et al. | 7,320,701 B2 | 1/2008 | Haut et al. |
| 6,500,195 | B2 | 12/2002 | Bonutti | 7,322,974 B2 | 1/2008 | Swoyer et al. |
| 6,506,190 | B1 | 1/2003 | Walshe | 7,334,822 B1 | 2/2008 | Hines et al. |
| 6,506,196 | B1 | 1/2003 | Laufer | 7,340,300 B2 | 3/2008 | Christopherson et al. |
| 6,517,569 | B2 | 2/2003 | Mikus et al. | 7,399,304 B2 | 7/2008 | Gambale et al. |
| 6,527,702 | B2 | 3/2003 | Whalen et al. | 7,402,166 B2 | 7/2008 | Feigl |
| 6,527,794 | B1 | 3/2003 | McDevitt et al. | 7,416,554 B2 | 8/2008 | Lam et al. |
| 6,530,932 | B1 | 3/2003 | Swayze et al. | 7,553,317 B2 | 6/2009 | Wesenburgh, II et al. |
| 6,533,796 | B1 | 3/2003 | Sauer et al. | 7,608,108 B2 | 10/2009 | Bhatnagar et al. |
| 6,547,725 | B1 | 4/2003 | Paolitto et al. | 7,658,311 B2 | 2/2010 | Boudreaux |
| 6,551,328 | B2 | 4/2003 | Kortenbach | 7,674,275 B2 | 3/2010 | Martin et al. |
| 6,551,333 | B2 | 4/2003 | Kuhns et al. | 7,727,248 B2 | 6/2010 | Smith et al. |
| 6,565,578 | B1 | 5/2003 | Peifer et al. | 2001/0044639 A1 | 11/2001 | Levinson |
| 6,569,187 | B1 | 5/2003 | Bonutti et al. | 2002/0095154 A1 | 7/2002 | Atkinson et al. |
| 6,572,626 | B1 | 6/2003 | Knodel et al. | 2002/0128684 A1 | 9/2002 | Foerster |
| 6,572,635 | B1 | 6/2003 | Bonutti | 2002/0161382 A1 | 10/2002 | Neisz et al. |
| 6,572,653 | B1 | 6/2003 | Simonson | 2002/0193809 A1 | 12/2002 | Meade et al. |
| 6,592,609 | B1 | 7/2003 | Bonutti | 2003/0109769 A1 | 6/2003 | Lowery et al. |
| 6,596,013 | B2 | 7/2003 | Yang et al. | 2003/0191497 A1 | 10/2003 | Cope |
| 6,599,311 | B1 | 7/2003 | Biggs et al. | 2003/0204195 A1 | 10/2003 | Keane et al. |
| 6,626,913 | B1 | 9/2003 | McKinnon et al. | 2004/0030217 A1 | 2/2004 | Yeung et al. |
| 6,626,916 | B1 | 9/2003 | Yeung et al. | 2004/0043052 A1 | 3/2004 | Hunter et al. |
| 6,626,919 | B1 | 9/2003 | Swanstrom | 2004/0078046 A1 | 4/2004 | Barzell et al. |
| 6,629,534 | B1 | 10/2003 | St. Goar et al. | 2004/0193191 A1 | 9/2004 | Starksen et al. |
| 6,641,592 | B1 | 11/2003 | Sauer et al. | 2004/0193194 A1 | 9/2004 | Laufer et al. |
| 6,656,182 | B1 | 12/2003 | Hayhurst | 2004/0194790 A1 | 10/2004 | Laufer et al. |
| 6,660,023 | B2 | 12/2003 | McDevitt et al. | 2004/0243178 A1 | 12/2004 | Haut et al. |
| 6,663,589 | B1 | 12/2003 | Halevy | 2004/0243179 A1 | 12/2004 | Foerster |
| 6,663,633 | B1 * | 12/2003 | Pierson, III ............... 606/148 | 2004/0243180 A1 | 12/2004 | Donnelly |
| 6,663,639 | B1 | 12/2003 | Laufer et al. | 2004/0243227 A1 | 12/2004 | Starksen et al. |
| 6,699,263 | B2 | 3/2004 | Cope | 2004/0260345 A1 | 12/2004 | Foerster |
| 6,706,047 | B2 | 3/2004 | Trout et al. | 2005/0055087 A1 | 3/2005 | Starksen |
| 6,709,493 | B2 | 3/2004 | DeGuiseppi et al. | 2005/0065550 A1 | 3/2005 | Starksen et al. |
| 6,715,804 | B2 | 4/2004 | Beers | 2005/0107811 A1 | 5/2005 | Starksen et al. |
| 6,719,709 | B2 | 4/2004 | Whalen et al. | 2005/0107812 A1 | 5/2005 | Starksen et al. |
| 6,730,112 | B2 | 5/2004 | Levinson | 2005/0154401 A1 | 7/2005 | Weldon et al. |
| 6,736,823 | B2 | 5/2004 | Darois et al. | 2005/0177181 A1 | 8/2005 | Kagan et al. |
| 6,736,854 | B2 | 5/2004 | Vadurro et al. | 2005/0203344 A1 | 9/2005 | Orban, III et al. |
| 6,740,098 | B2 | 5/2004 | Abrams et al. | 2005/0203550 A1 | 9/2005 | Laufer et al. |
| 6,767,037 | B2 | 7/2004 | Wenstrom, Jr. | 2005/0216078 A1 | 9/2005 | Starksen et al. |
| 6,770,076 | B2 | 8/2004 | Foerster | 2005/0267405 A1 | 12/2005 | Shah |
| 6,773,438 | B1 | 8/2004 | Knodel et al. | 2005/0273138 A1 | 12/2005 | To et al. |
| 6,773,441 | B1 | 8/2004 | Laufer et al. | 2006/0025750 A1 | 2/2006 | Starksen et al. |
| 6,790,213 | B2 | 9/2004 | Cherok et al. | 2006/0025784 A1 | 2/2006 | Starksen et al. |
| 6,802,846 | B2 | 10/2004 | Hauschild et al. | 2006/0025789 A1 | 2/2006 | Laufer et al. |
| 6,821,282 | B2 | 11/2004 | Perry et al. | 2006/0025819 A1 | 2/2006 | Nobis et al. |
| 6,821,285 | B2 | 11/2004 | Laufer et al. | 2006/0030884 A1 | 2/2006 | Yeung et al. |
| 6,821,291 | B2 | 11/2004 | Bolea et al. | 2006/0058817 A1 | 3/2006 | Starksen et al. |

| | | | |
|---|---|---|---|
| 2006/0089646 A1 | 4/2006 | Bonutti | |
| 2006/0167477 A1 | 7/2006 | Arcia et al. | |
| 2006/0265042 A1 | 11/2006 | Catanese, III et al. | |
| 2006/0282081 A1 | 12/2006 | Fanton et al. | |
| 2007/0049929 A1 | 3/2007 | Catanese, III | |
| 2007/0049970 A1 | 3/2007 | Belef et al. | |
| 2007/0060931 A1 | 3/2007 | Hamilton et al. | |
| 2007/0088362 A1 | 4/2007 | Bonutti et al. | |
| 2007/0112385 A1 | 5/2007 | Conlon | |
| 2007/0142846 A1 | 6/2007 | Catanese, III et al. | |
| 2007/0173888 A1 | 7/2007 | Gertner et al. | |
| 2007/0260259 A1 | 11/2007 | Fanton et al. | |
| 2008/0009888 A1 | 1/2008 | Ewers et al. | |
| 2008/0021445 A1 | 1/2008 | Elmouelhi et al. | |
| 2008/0033488 A1 | 2/2008 | Catanese, III et al. | |
| 2008/0039894 A1 | 2/2008 | Catanese, III et al. | |
| 2008/0045978 A1 | 2/2008 | Kuhns et al. | |
| 2008/0058710 A1 | 3/2008 | Wilk | |
| 2008/0065120 A1 | 3/2008 | Zannis et al. | |
| 2008/0082113 A1 | 4/2008 | Bishop et al. | |
| 2008/0086172 A1 | 4/2008 | Martin et al. | |
| 2008/0091220 A1 | 4/2008 | Chu | |
| 2008/0091237 A1 | 4/2008 | Schwartz et al. | |
| 2008/0119874 A1 | 5/2008 | Merves | |
| 2008/0154378 A1 | 6/2008 | Pelo | |
| 2008/0195145 A1 | 8/2008 | Bonutti et al. | |
| 2008/0208220 A1 | 8/2008 | Shiono et al. | |
| 2009/0012537 A1 | 1/2009 | Green | |
| 2010/0010631 A1 | 1/2010 | Otte et al. | |
| 2010/0114162 A1 | 5/2010 | Bojarski et al. | |
| 2010/0286106 A1 | 11/2010 | Gat et al. | |
| 2010/0286679 A1 | 11/2010 | Hoey et al. | |

FOREIGN PATENT DOCUMENTS

| | | |
|---|---|---|
| EP | 0464480 | 1/1992 |
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| JP | 9122134 | 5/1997 |
| JP | 2004344427 | 12/2004 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO9210142 | 6/1992 |
| WO | WO9304727 | 3/1993 |
| WO | WO9315664 | 8/1993 |
| WO | WO0230335 | 4/2002 |
| WO | WO03039334 | 5/2003 |
| WO | WO03077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008043917 | 4/2008 |
| WO | WO2009009617 | 1/2009 |
| WO | WO2010011832 | 1/2010 |

OTHER PUBLICATIONS

P. Schauer et al., "New applications for endoscopy: the emerging field of endoluminal and transgastric bariatric surgery," Surgical Endoscopy, Accepted Jun. 7, 2006.

Richard Berges et al., "Alternative Minimalinvasive Therapien Beim Benignen Prostatasyndrom", medizin, Jg, 104 heft 37, Sep. 14, 2007.

Rudolf Hartung, et al., Instrumentelle Therapie der benegnen Prostatahyperplasie, Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 194(36): A2424-9.

R. Hubmann, Geschichte der transurethralen Prostataeingriffe, Geschichte der Medizin, Urologe B} 2000 40: 152-160.

U. Jonas, et al. Benigne Prostatahyperplasie, Der Urologe 2006, [Sonderheft] 45: 134-144.

O.A. Bacharova, et al. "The Effect of Rhodiolae Rosea Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 209; 16 (1): 19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8 No. 8, p. 35-39.

O. Reich, et al., "Benignes Prostatasyndrom (BPS)", er Urologe A Issue vol. 45, No. 6, Jun. 2006, p. 769-782.

Daito Takashi, "Low-Invasive Treatment for BPH", Medico vol. 34, No. 10 p. 366-369.

Trapeznikov et al., "New Technologies in the Treatment of Benign Prostatic Hyperplasia", Urologia Nefrol (Mosk) Jul.-Aug. 1996, (4): 41-47.

Koyanagi Tomohiko, et al., "Surgery View of 21st Century", Urological Surgery, vol. 84, No. 1 p. 47-53.

Borzhievski et al., "Tactics of the Surgical Treatment of Patients With Prostatic Adenoma and Acute Urinary Retention", Urologia Nefrol (Mosk). Jan.-Feb. 1987, (1): 39-43.

Yeung, Jeff, "Treating Urinary Stress Incontinence Without Incision with Endoscopic Suture Anchor & Approximating Device," Aleeva Medical, Inc., 2007.

* cited by examiner

COILED ANCHOR DEVICE

CROSS-REFERENCE TO RELATED APPLICATIONS

This application is a continuation-in-part of: 1) U.S. patent application Ser. No. 12/852,243, now U.S. Pat. No. 8,333,776, filed Aug. 6, 2010; 2) U.S. patent application Ser. No. 12/521,674, now U.S. Pat. No. 8,216,254, filed Jul. 30, 2009 which claims the benefit of Provisional Application Ser. No. 61/084,937; 3) U.S. patent application Ser. No. 11/775,162, filed Jul. 9, 2007: 4) U.S. patent application Ser. No. 11/671,914, now U.S. Pat. No. 8,157,815, filed Feb. 6, 2007; 5) U.S. patent application Ser. No. 11/492,690, now U.S. Pat. No. 7,896,891, filed on Jul. 24, 2006; 6) U.S. patent application Ser. No. 11/833,660, filed on Aug. 3, 2007, which is a continuation of U.S. patent application Ser. No. 11/318,246, now U.S. Pat. No. 7,645,286, filed on Dec. 22, 2005; and 7) U.S. patent application Ser. No. 11/838,036, now U.S. Pat. No. 7,914,542, filed on Aug. 13, 2007, which is a continuation of U.S. patent application Ser. No. 11/134,870, now U.S. Pat. No. 7,758,594, filed on May 20, 2005; the entire disclosures of each of which are expressly incorporated herein by reference.

FIELD OF THE INVENTION

The disclosed embodiments relate generally to medical devices and methods, and more particularly to systems and associated methods for manipulating or retracting tissues and anatomical or other structures within the body of human or animal subjects for the purpose of treating diseases or disorders.

BACKGROUND

There are a wide variety of situations in which it is desirable to lift, compress or otherwise reposition normal or aberrant tissues or anatomical structures (e.g., glands, organs, ligaments, tendons, muscles, tumors, cysts, fat pads, and the like) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, and the like) and/or for cosmetic purposes (e.g., face lifts, breast lifts, brow lifts, and the like) and/or for research and development purposes (e.g., to create animal models that mimic various pathological conditions). In many of these procedures, surgical incisions are made in the body, and laborious surgical dissection is performed to access and expose the affected tissues or anatomical structures. Thereafter, in some cases, the affected tissues or anatomical structures are removed or excised. In other cases, various natural or man-made materials are used to lift, sling, reposition or compress the affected tissues.

Benign Prostatic Hyperplasia (BPH):

One example of a condition where it is desirable to lift, compress or otherwise remove a pathologically enlarged tissue is Benign Prostatic Hyperplasia (BPH). BPH is one of the most common medical conditions that affects men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH is expected to increase as the average age of the population increases in developed countries.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus, the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate, and the like.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine, and the like) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Medications for treating BPH symptoms include phytotherapy and prescription medications. In phytotherapy, plant products such as Saw Palmetto, African Pygeum, Serenoa Repens (sago palm) and South African star grass are administered to the patient. Prescription medications are prescribed as first line therapy in patients with symptoms that are interfering with their daily activities. Two main classes of prescription medications are alpha-1 a-adrenergic receptors blockers and 5-alpha-reductase inhibitors. Alpha-1 a-adrenergic receptors blockers block the activity of alpha-1 a-adrenergic receptors that are responsible for causing constriction of smooth muscle cells in the prostate. Thus, blocking the activity of alpha-1 a-adrenergic receptors causes prostatic smooth muscle relaxation. This, in turn, reduces urethral resistance thereby reducing the severity of the symptoms. 5-alpha-reductase inhibitors block the conversion of testosterone to di-hydro-testosterone. Di-hydro-testosterone causes growth of epithelial cells in the prostate gland. Thus, 5-alpha-reductase inhibitors cause regression of epithelial cells in the prostate gland and, hence, reduce the volume of the prostate gland, which in turn reduces the severity of the symptoms.

Surgical procedures for treating BPH symptoms include Transurethral Resection of Prostate (TURP), Transurethral Electrovaporization of Prostate (TVP), Transurethral Incision of the Prostate (TUIP), Laser Prostatectomy and Open Prostatectomy.

Transurethral Resection of Prostate (TURP) is the most commonly practiced surgical procedure implemented for the treatment of BPH. In this procedure, prostatic urethral obstruction is reduced by removing most of the prostatic urethra and a sizeable volume of the surrounding prostate gland. This is carried out under general or spinal anesthesia. In this procedure, a urologist visualizes the urethra by inserting a resectoscope, that houses an optical lens in communication with a video camera, into the urethra such that the distal region of the resectoscope is in the region of the urethra surrounded by the prostate gland. The distal region of the resectoscope consists of an electric cutting loop that can cut prostatic tissue when an electric current is applied to the device. An electric return pad is placed on the patient to close the cutting circuit. The electric cutting loop is used to scrape away tissue from the inside of the prostate gland. The tissue that is scraped away is flushed out of the urinary system using an irrigation fluid. Using a coagulation energy setting, the loop is also used to cauterize transected vessels during the operation.

Another example of a surgical procedure for treating BPH symptoms is Transurethral Electrovaporization of the Prostate (TVP). In this procedure, a part of prostatic tissue squeezing the urethra is desiccated or vaporized. This is carried out under general or spinal anesthesia. In this procedure, a resectoscope is inserted transurethrally such that the distal region of the resectoscope is in the region of the urethra surrounded by the prostate gland. The distal region of the resectoscope consists of a rollerball or a grooved roller electrode. A controlled amount of electric current is passed through the electrode. The surrounding tissue is rapidly heated up and vaporized to create a vaporized space. Thus, the region of the urethra that is blocked by the surrounding prostate gland is opened up.

Another example of a surgical procedure for treating BPH symptoms is Transurethral Incision of the Prostate (TUIP). In this procedure, the resistance to urine flow is reduced by making one or more incisions in the prostate gland in the region where the urethra meets the urinary bladder. This procedure is performed under general or spinal anesthesia. In this procedure, one or more incisions are made in the muscle of the bladder neck, which is the region where the urethra meets the urinary bladder. The incisions are in most cases deep enough to cut the surrounding prostate gland tissue including the prostatic capsule. This releases any compression on the bladder neck and causes the bladder neck to spring apart. The incisions can be made using a resectoscope, laser beam, and the like.

Another example of a surgical procedure for treating BPH symptoms is Laser Prostatectomy. Two common techniques used for Laser Prostatectomy are Visual Laser Ablation of the Prostate (VLAP) and the Holmium Laser Resection/Enucleation of the Prostate (HoLEP). In VLAP, a neodymium: Yttrium-aluminum-garnet (NdYAG) laser is used to ablate tissue by causing coagulation necrosis. The procedure is performed under visual guidance. In HoLEP, a holmium: Yttrium-aluminum-garnet laser is used for direct contact ablation of tissue. Both these techniques are used to remove tissue obstructing the urethral passage to reduce the severity of BPH symptoms.

Another example of a surgical procedure for treating BPH symptoms is Photoselective Vaporization of the Prostate (PVP). In this procedure, laser energy is used to vaporize prostatic tissue to relieve obstruction to urine flow in the urethra. The type of laser used is the lithium triborate (LBO) laser. The wavelength of this laser is highly absorbed by oxyhemoglobin. This laser vaporizes cellular water and, hence, is used to remove tissue that is obstructing the urethra.

Another example of a surgical procedure for treating BPH symptoms is Open Prostatectomy. In this procedure, the prostate gland is surgically removed by an open surgery. This is done under general anesthesia. The prostate gland is removed through an incision in the lower abdomen or the perineum. The procedure is used mostly in patients that have a large (greater than approximately 100 grams) prostate gland.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland, thus, reducing the severity of BPH symptoms.

Another example of a minimally invasive procedure for treating BPH symptoms is Transurethral Needle Ablation (TUNA). In this procedure, heat-induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radiofrequency needles that emerge at an angle of 90 degrees from the delivery catheter. The two radiofrequency needles are aligned at an angle of 40 degrees to each other so that they penetrate the lateral lobes of the prostate. A radiofrequency current is delivered through the radiofrequency needles to heat the tissue of the lateral lobes to 70-100 degree Celsius at a radiofrequency power of approximately 456 KHz for approximately 4 minutes per lesion. This creates coagulation defects in the lateral lobes. The coagulation defects cause shrinkage of prostatic tissue which in turn reduces the degree of squeezing of the urethra by the prostate gland thus reducing the severity of BPH symptoms.

Another example of a minimally invasive procedure for treating BPH symptoms is Interstitial Laser Coagulation (ILC). In this procedure, laser-induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra, and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy 360° along the terminal 3 mm of the laser fiber. The distal tip is inserted into the middle lobe of the prostate gland, and laser energy is delivered through the distal tip for a desired time. This heats the middle lobe and causes laser-induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which, in turn, causes the prostate gland to shrink. Shrinkage of the prostate gland reduces the degree of squeezing of the urethra by the prostate, thus, reducing the severity of BPH symptoms.

Another example of a minimally invasive procedure for treating BPH symptoms is implanting Prostatic Stents. In this procedure, the region of urethra surrounded by the prostate is mechanically supported to reduce the constriction caused by an enlarged prostate. Prostatic stents are flexible devices that are expanded after their insertion in the urethra. They mechanically support the urethra by pushing the obstructing prostatic tissue away from the urethra. This reduces the constriction of the urethra and improves urine flow past the prostate gland thereby reducing the severity of BPH symptoms.

Although existing treatments provide some relief to the patient from symptoms of BPH, they have disadvantages. Alpha-1 a-adrenergic receptors blockers have side effects such as dizziness, postural hypotension, lightheadedness, asthenia and nasal stuffiness. Retrograde ejaculation can also occur. 5-alpha-reductase inhibitors have minimal side effects, but only have a modest effect on BPH symptoms and the flow rate of urine. In addition, anti-androgens, such as 5-alpha-reductase, require months of therapy before LUTS improvements are observed. Surgical treatments of BPH carry a risk of complications including erectile dysfunction; retrograde ejaculation; urinary incontinence; complications related to anesthesia; damage to the penis or urethra; need for a repeat surgery; and the like. Even TURP, which is the gold standard in treatment of BPH, carries a high risk of complications. Adverse events associated with this procedure are reported to include retrograde ejaculation (65% of patients), post-operative irritation (15%), erectile dysfunction (10%), need for transfusion (8%), bladder neck constriction (7%), infection (6%), significant hematuria (6%), acute urinary retention (5%), need for secondary procedure (5%), and incontinence (3%). Typical recovery from TURP involves several days of inpatient hospital treatment with an indwelling urethral catheter, followed by several weeks in which obstructive symptoms are relieved, but there is pain or discomfort during micturition.

The reduction in the symptom score after minimally invasive procedures is not as large as the reduction in symptom score after TURP. Up to 25% of patients who receive these minimally invasive procedures ultimately undergo a TURP within 2 years. The improvement in the symptom score generally does not occur immediately after the procedure. For example, it takes an average of one month for a patient to notice improvement in symptoms after TUMT and 1.5 months to notice improvement after ILC. In fact, symptoms are typically worse for these therapies that heat or cook tissue, because of the swelling and necrosis that occurs in the initial weeks following the procedures. Prostatic stents often offer more immediate relief from obstruction but are now rarely used because of high adverse effect rates. Stents have the risk of migration from the original implant site (up to 12.5% of patients), encrustation (up to 27.5%), incontinence (up to 3%), and recurrent pain and discomfort. In published studies, these adverse effects necessitated 8% to 47% of stents to be explanted. Overgrowth of tissue through the stent and complex stent geometries has made their removal quite difficult and invasive.

Thus, the most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and, in fact, often experiences worse symptoms for weeks after the procedure until the body begins to heal. Additionally, all device approaches require a urethral catheter placed in the bladder, and in some cases for weeks. In some cases, catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Cosmetic or Reconstructive Tissue Lifting and Repositioning:

Many cosmetic or reconstructive surgical procedures involve lifting, compressing or repositioning of natural tissue, natural tissue or artificial grafts, or aberrant tissue. For example, surgical procedures such as face lifts, brow lifts, neck lifts, tummy tucks, and the like, have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin, and then attaching the repositioned tissues to underlying or nearby structures (e.g., bone, periostium, or other muscles) to hold the repositioned tissues in their new (e.g., lifted) position. In some cases, excess skin may also be removed during the procedure.

There have been attempts to develop minimally invasive devices and methods for cosmetic lifting and repositioning of tissues. For example, connector suspension lifts have been developed where one end of a standard or modified connector thread is attached to muscle and the other end is anchored to bone, periostium or another structure to lift and reposition the tissues as desired. Some of these connector suspension techniques have been performed through cannulas or needles inserted though relatively small incisions of puncture wounds.

There remains a need for the development of a suture lock or suture anchor that can be used throughout the body. The disclosed embodiments address these and other needs.

SUMMARY

Briefly and in general terms, the disclosed embodiments are directed towards anchor assemblies for positioning within a patient's body. In one particular aspect, the disclosed embodiments are directed towards an anchor assembly, which includes a first or distal anchor assembly component that is deployed at a first location within a patient's body, and a second or proximal anchor assembly component that is deployed at a second location within the patient. The device also accomplishes imparting a tension between implanted anchor components.

In one aspect, the second or proximal anchor assembly component includes a coiled portion intended to receive and lock onto a connector. The coiled portion can extend an entire or a portion of a length of the second anchor. Moreover, the second anchor can have a pitch that varies along its length and can include a pitch that decreases from a first end to a midsection. The second anchor can further include first and second overlapping coiled portions, the termination of one coiled portion defining a space for receiving the connector. Further, the second anchor can include a tubular portion connected to a coiled portion, the tubular and coiled portions defining a longitudinal bore for receiving a connector. In other contemplated approaches, coiled structures cooperate with additional subassemblies to define the anchor.

Furthermore, in one embodiment the anchor assembly includes a distal anchor for securing to a suture connector as part of a distal end of the anchor system. The distal anchor includes a generally tubular head portion, a mid-section transitioning from the head portion, and a tail portion, wherein the tail portion is connected to the mid-section via a connector section. The connector section acts as a spring to create a relative unconstrained laterally oriented configuration between the head portion and the tail portion. The tail portion embodies structure having a surface area that is larger than the connector section to provide a substantial platform for engaging tissue at a target site. In one particular approach, a body of the distal anchor includes a coiled portion extending from which is a tail.

Other features and advantages will become apparent from the following detailed description, taken in conjunction with the accompanying drawings, which illustrate by way of example, the features of the various embodiments.

DETAILED DESCRIPTION

Figure 1A:
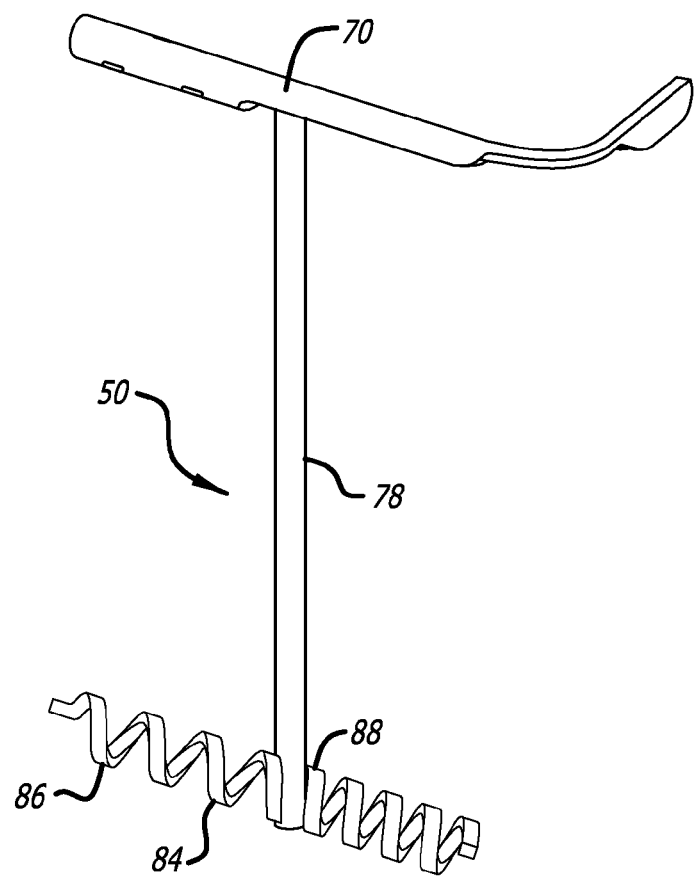
FIGS. 1A-B are perspective views of one embodiment of an anchor assembly that includes a distal anchor and a proximal anchor secured together by a suture and a delivery device for assembling the anchor assembly.

Turning now to the figures, which are provided by way of example and not limitation, the disclosed embodiments are illustrated with regard to anchor assemblies configured to be delivered within a patient's body. As stated, the disclosed embodiments can be employed for various medical purposes including but not limited to approximating, retracting, lifting, compressing, supporting or repositioning tissues, organs, anatomical structures, grafts or other material found within a patient's body. Such tissue manipulation is intended to facilitate the treatment of diseases or disorders. Moreover, the disclosed embodiments have applications in cosmetic or reconstruction purposes, or in areas relating to the development or research of medical treatments.

In such applications, one portion of an anchor assembly is positioned and implanted against a first section of anatomy. A second portion of the anchor assembly is then positioned and implanted adjacent to a second section of anatomy for the purpose of approximating, retracting, lifting, compressing, supporting or repositioning one section of anatomy with respect to the other section of anatomy, as well as for the purpose of approximating, retracting, lifting, compressing, supporting or repositioning one section of anatomy with respect to the other section of anatomy. It is also to be recognized that both a first and second portion of the anchor assembly can be configured to accomplish the desired approximating, retracting, lifting, compressing, supporting or repositioning of anatomy due to tension supplied thereto via a connector assembly (e.g., suture) affixed to the first and second portions of the anchor assembly.

In one embodiment of the anchor assembly, the anchor assembly is configured to include structure that is capable of being implanted within a patient's body. The anchor assembly may also be used in conjunction with a conventional remote viewing device (e.g., an endoscope) so that an interventional site can be observed.

In one aspect, the anchor assembly can be placed at an intervention site using a delivery tool. One specific, non-limiting application of the delivery tool is for the treatment of benign prostatic hyperplasia. In this procedure, an implant is delivered to a prostatic lobe that is obstructing the urethral opening and restricting flow. The implant compresses the lobe, thereby increasing the urethral opening and reducing the fluid obstruction through the prostatic urethra.

Referring now to the drawings, wherein like reference numerals denote like or corresponding components throughout the drawings and, more particularly to FIGS. 1A-4C, there is shown an embodiment of an anchor assembly. Accordingly, in one embodiment, the anchor assembly 50 is embodied in a tissue approximation anchor (TAA). The tissue approximation anchor is an implant assembly that includes one tubular member, referred to as the capsular anchor or, more generally, distal anchor 70. The distal anchor 70 is preferably connected by a suture (preferably polyester) 78 to an urethral anchor or proximal anchor 84. In one specific, non-limiting embodiment, the distal anchor 70 is comprised of an electro-polished Nitinol (nickel titanium alloy SE508, 55.8% nickel) tube.

The tissue approximation anchor is designed to be useable in an office environment (in contrast to requiring a hospital environment). The delivery tool is used through a 19 Fr introducer sheath size in one preferred embodiment, while in another embodiment a sheath size of 21 F is employed. Additionally, the material selection and construction of the tissue approximation anchor still allows for a subsequent TURP procedure to be performed, if necessary. In this suture-based, tissue approximation technique, a needle delivery mechanism is used to implant a nitinol distal anchor 70 and attached connector or suture 78. In one approach, the introducer sheath is first placed within a patient's urethra. An anchor housed within the delivery tool is then placed through the introducer sheath and a distal portion of the delivery tool is placed at the interventional site. Once the distal anchor 70 and attached suture 78 have been deployed, with the needle retracted and the suture 78 tensioned, the anchor 84 is pushed by the delivery tool and captures the suture 78 transverse to the anchor axis.

In one embodiment, the nitinol tube is attached to a USP size 0 PET (Poly Ethylene Terephthalate) monofilament suture 78 by thermally forming the suture to locking features on the anchor 70. Referring again to the suture itself, the PET suture is a round monofilament extrusion/pulltrusion composed of a grade 8816 polyethylene terephthalate. Typically, the base material for the suture is annealed at approximately 191 degrees Celsius for approximately 5 minutes in a straight condition. In one non-limiting embodiment, the PET suture 78 has a diameter of 0.015 inches and a tensile strength greater than or equal to 6.0 pounds.

The proximal anchor 84 can embody a flat stainless steel wound coil (0.0086 inches×0.0155 inches) with a 0.040 inch outer diameter. One end portion 86 of the anchor 84 can have an elongated pitch that decreases along a length of the anchor toward its mid-section 88. The mid-section 88 can include coils intended to lockingly grasp the connector 78.

Figure 2:
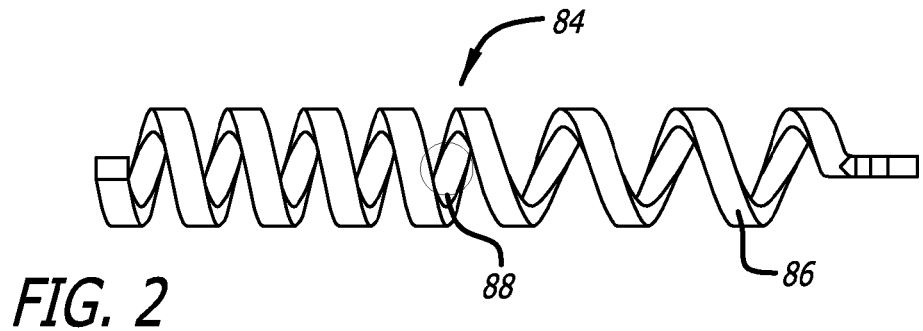
FIG. 2 is an enlarged view of the coiled anchor shown in FIG. 1.

Thus, as best seen in FIG. 2, the proximal anchor 84 can embody a two pitch or a progressive pitch coil having a greater pitch at a first end 86. The greater pitch facilitates feeding a connector 78 between winds until the connector 78 is fixed between adjacent coils (See FIGS. 4A-C). In one approach, a reduced pitch section of the anchor 84 compresses and locks the connector 78 midway 88 in the anchor 84.

Figure 1B:
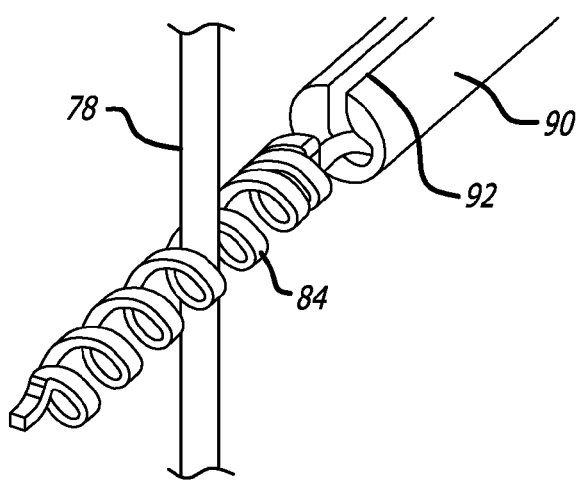
Figure 4A:
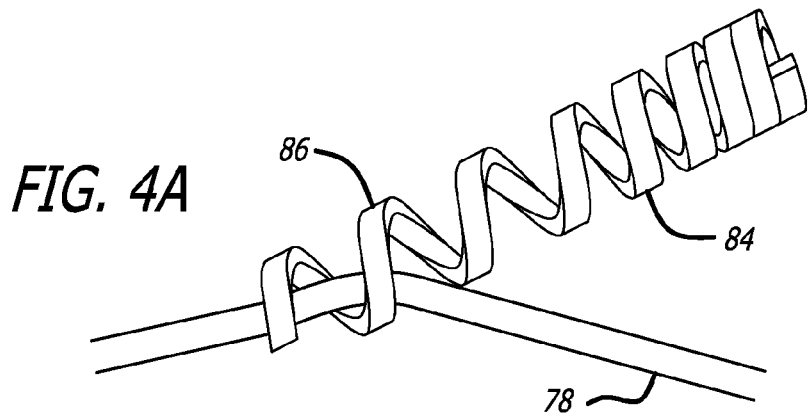
FIGS. 4A-C are perspective views of turning the coiled anchor of FIG. 1 onto a connector.
Figure 4B:
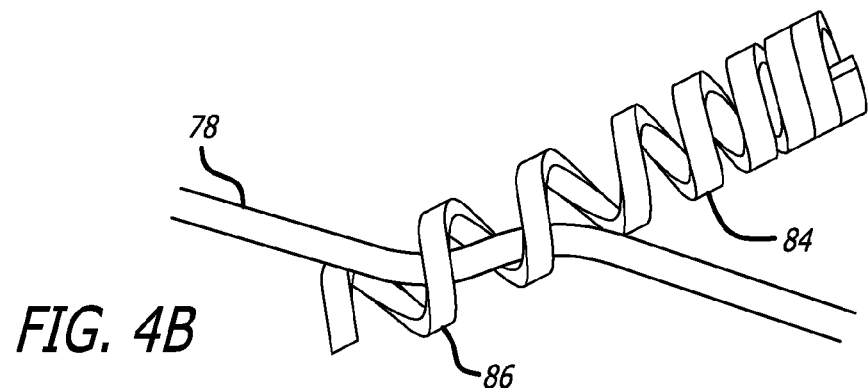
Figure 4C:
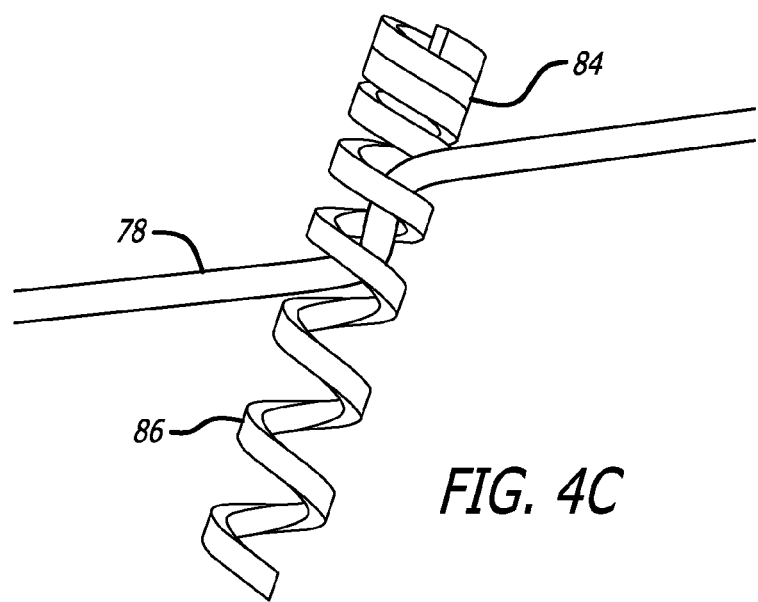

It is contemplated that a rotational actuation 90 can be employed to attach a proximal anchor 84 to a connector 78 (See FIG. 1B). The actuator 90 can include a slot 92 for registering the anchor 84 and to torque the anchor 84 along the connector (FIGS. 4A-C). A fixed internal or external comb (not shown) guides the coils of the anchor forward as the device is rotated much like a bolt in a nut. The relative positioning of the actuator 90 and anchor 84 are arranged such that the anchor 84 should fully seat and firmly attach to a connector 78 before the anchor 84 is released from the actuator 90. Once this juxtapositional relationship is achieved, the anchor 84 is immediately released from the actuator 90.

Figure 3A:
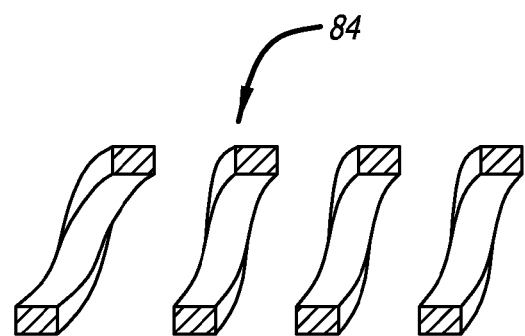
FIG. 3A is a cross section of the coiled anchor of FIG. 1.
Figure 3B:
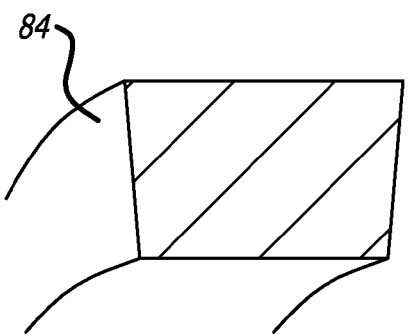
FIG. 3B is an enlarged cross section view of a portion of the coiled anchor of FIG. 3A.

With specific reference now to FIGS. 3A-B, one cross-sectional profile of the coils of a proximal anchor is depicted. A flat wire or shaped wire is contemplated to increase line contact and increase pressure on a connector to which the anchor 84 is affixed. Thus, the anchor 84 presents a biting edge which resists a pull-off force which may be applied to the connector.

Figure 5:
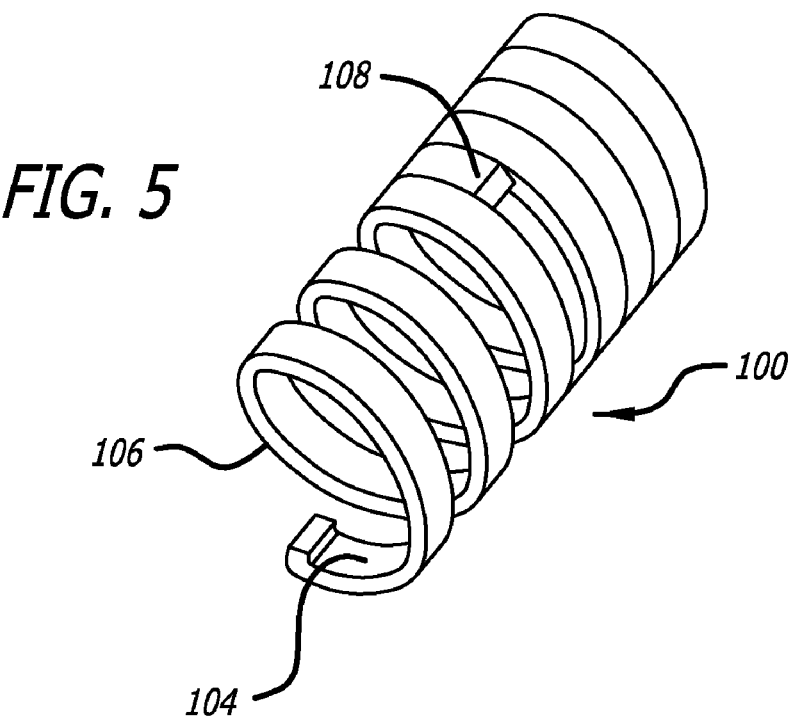
FIG. 5 is a perspective view of another embodiment of a coiled anchor.
Figure 6:
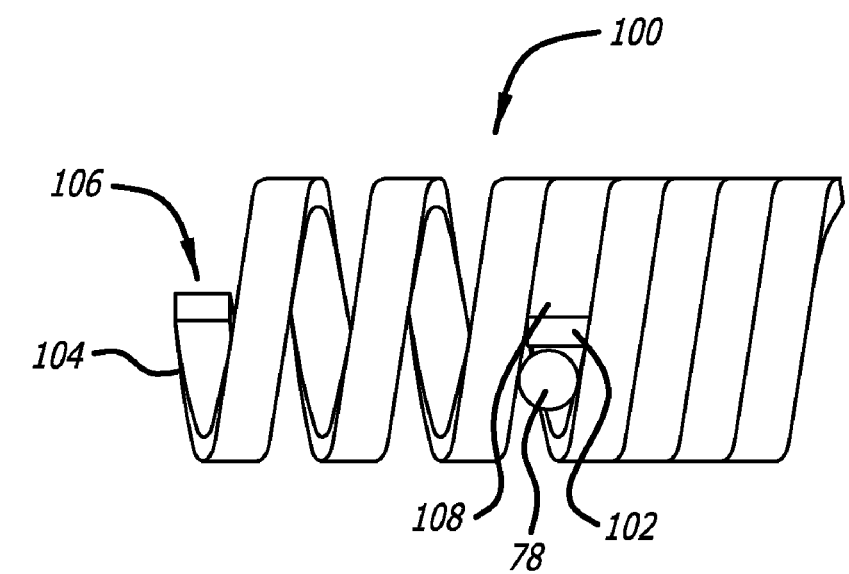
FIG. 6 is a side enlarged view of the coiled anchor of FIG. 5.

Turning now to FIGS. 5 and 6, there is shown an alternative approach to a coiled anchor 100. Here, the anchor 100 defines a self locking coil structure embodying a folded-over wire. The anchor is formed by bifilar winding two wires over a mandrel to create a closed pitch coil with first 102 and second 104 wire ends terminating at unique points along the anchor 100. That is, one end 104 may terminate at a distal end 106 of the anchor 100 and another end 102 terminating midway 108 along the length of the device. The middle wire termination 108 may be bent in a direction that would allow a connector 78 to be engaged by the coil and torqued to the middle point 108 of the anchor 100. The connector 78 would thus pass across the middle wire termination 102. The orientation of the middle wire termination 102 would, in turn, prevent the connector 78 from winding back out of the anchor structure.

Figure 7A:
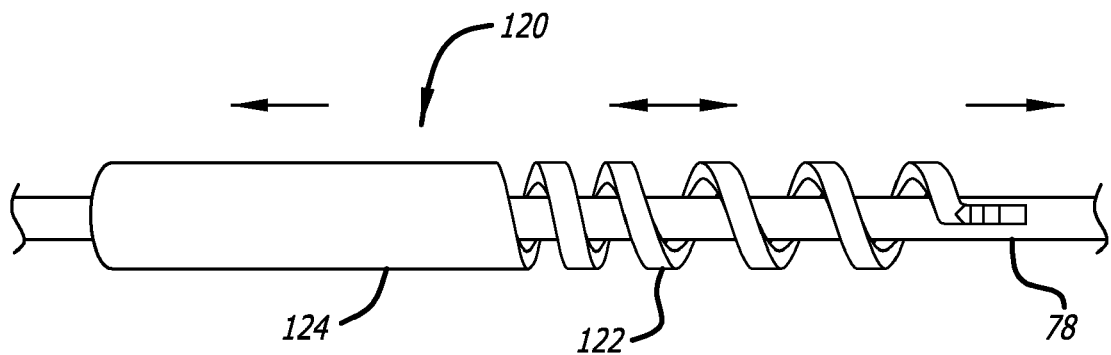
FIGS. 7A-B are side views, depicting another approach to a coiled anchor.
Figure 7B:
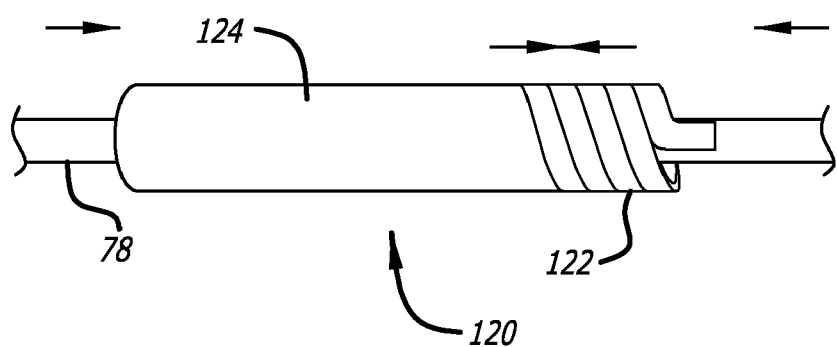

Yet another contemplated approach to a coiled anchor 120 is shown in FIGS. 7A-B. The coiled anchor 120 can be placed in a coaxial arrangement with a connector 78. The coiled anchor 120 is first placed on a connector in a condition where adjacent coils are displaced longitudinally (FIG. 7A). The adjacent coils are then permitted to collapse longitudinally to thereby fixedly capture the connector 78.

In one contemplated embodiment, the coiled anchor 120 can have a proximal coiled portion 122 connected to a distal tubular section 124. The proximal coiled portion 122 can define a pigtail configuration that when longitudinally expanded, permits the sliding of the anchor 120 along a connector 78. The distal tubular section 122 includes an internal bore which also slidingly receives the connector. Upon approximation of tissue, the pigtail structure is permitted to contract and thereby bite into and lock with connector material and define a closed coil structure.

Figure 8A:
FIGS. 8A-C are perspective views, depicting approaches to a coiled anchor assembly.
Figure 8B:
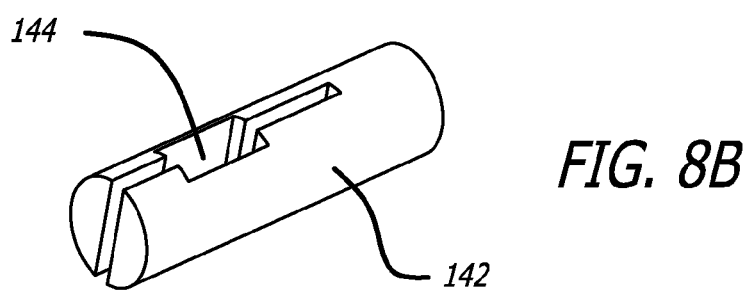
Figure 8C:
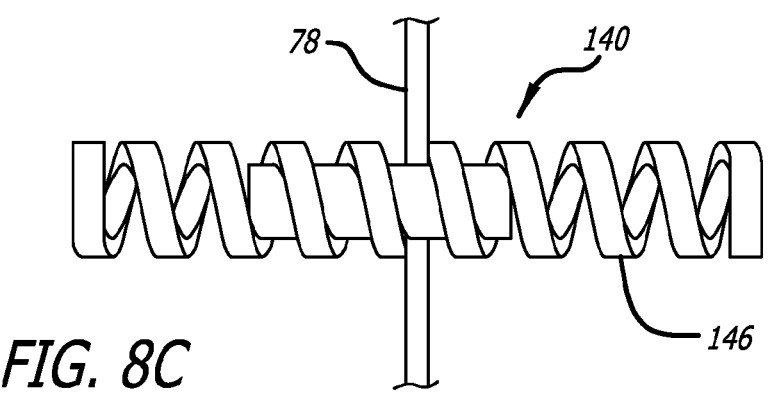

A coil and slug approach 140 to a proximal anchor can also be employed in a tissue approximation interventional procedure. In this embodiment, a slug 142 having a longitudinal slot 144 sized to accept and lock onto a connector is contemplated to be placed within a bore defined by a coiled outer member 146. The plug 142 can be positioned within a distal opening 148 to the internal bore of the coiled outer member 146 (See FIG. 8A) and configured to receive the connector 78 within its slotted structure 144. As the coiled outer member 146 is threaded along the connector 78 the slug is turned and translated further within the internal bore of the coiled outer member 146. Upon reaching a midsection of the assembly, the connector 78 is locked in placed as described above.

The coil and slug approach 140 is intended to address urine retention when the assembly is used in a prostate interventional procedure. That is, urine retention can be reduced from the open coiled structure by filling the void with the plug. In addition to filling the void, it is contemplated that the slot 144 formed in the slug 142 can assume a profile enveloping connector material. Further, the slot can extend approximately half the length of the slug to define arms adapted to conveniently receive the connector.

Figure 9A:
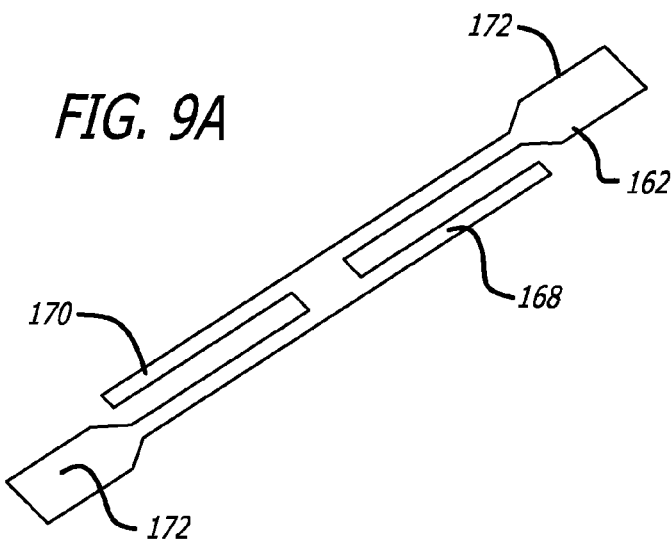
FIGS. 9A-C are side views, depicting yet further approaches to a coiled anchor assembly.
Figure 9B:
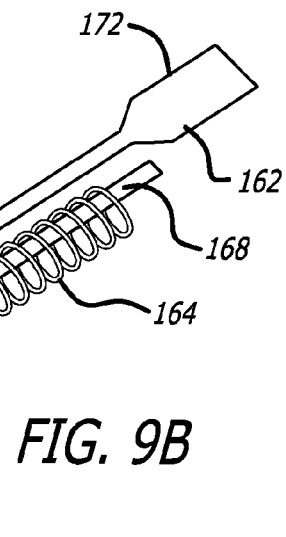
Figure 9C:
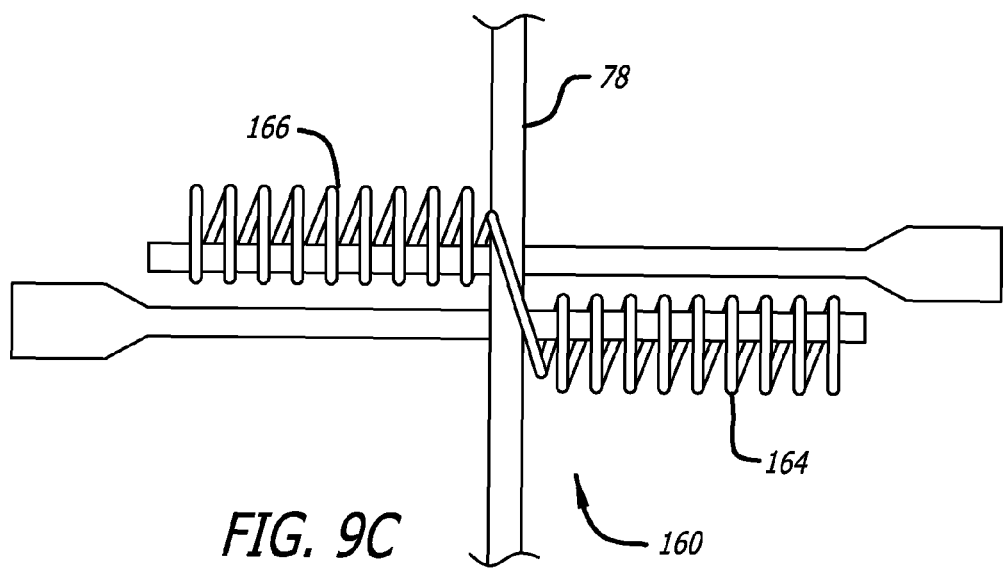

In yet another embodiment (See FIGS. 9 A-C), the proximal anchor 160 can embody a flat cut elongated substruction 162 configured to receive first 164 and second 166 coils. The first and second coils 164, 166 are configured about first 168 and second 170 arms of the substructure 162 such that the coils extend both distally and proximally of a midpoint of the substructure 162. At proximal and distal ends of the substructure 162 are paddles 172 which function to limit central portions of the coils which can in certain applications define overlapping structure. The portions of the coils 164, 166 extending along the substructure 162 can be unique or symmetrical. Further, the coils 164, 166 can be pre-cut or shaped to a tissue-friendly load distributing 2D-shape. A distal paddle 172 can be configured to extend past the connector 78 and the assembly 160 can be rotated until the connector 78 is engaged and captured within the coil windings. In this way, the connector 78 would be locked in a transverse orientation to the anchor 160.

Figure 10A:
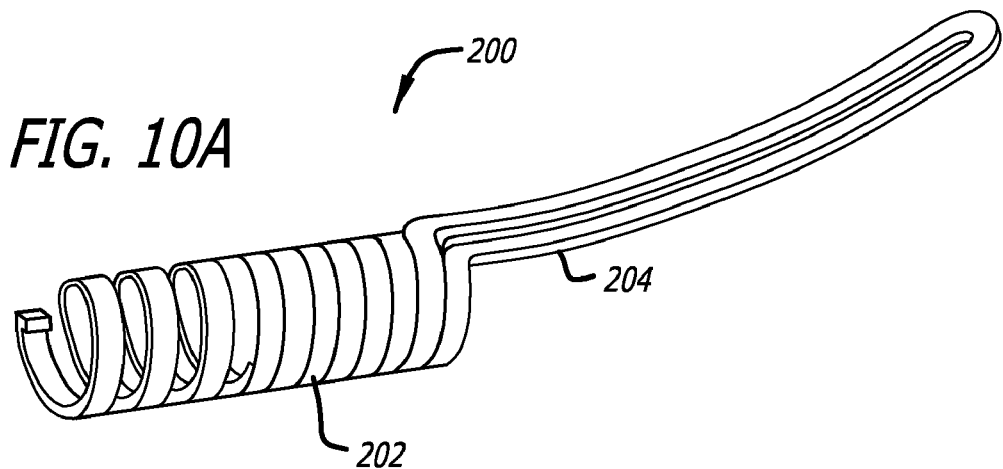
FIGS. 10A-C are perspective views, depicting an approach to a coiled distal anchor.
Figure 10B:
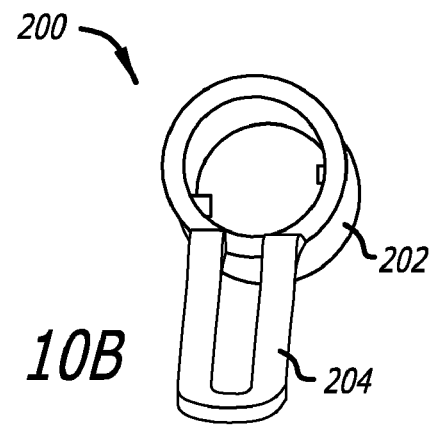
Figure 10C:
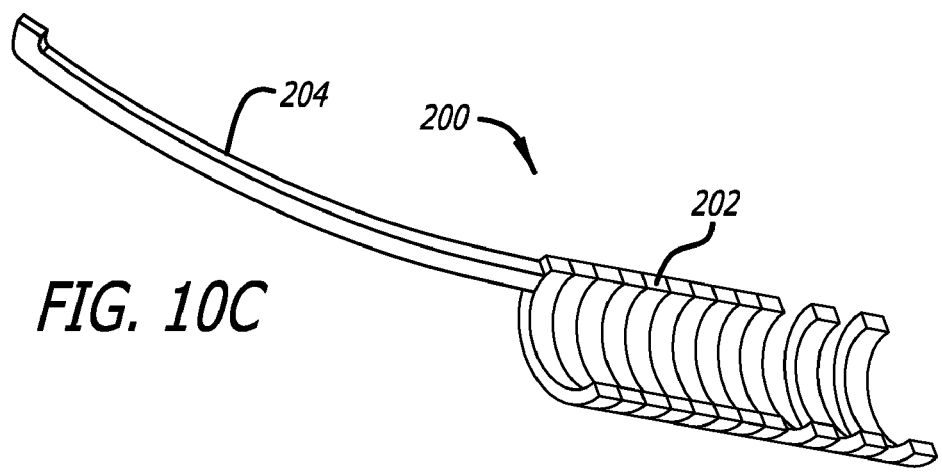

One alternative approach to a distal anchor 200 is depicted in FIGS. 10A-C. In this embodiment, the anchor 200 includes both a body 202 and a tail 204 formed by a wire. The structures can be polymer coated or can further include an overmolded element which increases rigidity of locking coils together. It is also contemplated that the connector can further be configured as part of the overmolded element. The body 202 is defined by a coiled section of the wire and the tail is defined by a looped section of the wire. The body 202 thus has a spring-like longitudinal resiliency and can be sized to fixedly engage a connector. As shown, the body 202 can define coils having a variable pitch. The tail 204 is generally curved longitudinally to facilitate anchoring functioning of the device.

Thus, in its pre-implanted form, the anchor assembly can include a distal anchor 70 (e.g., first anchor) whose initial engagement with a suture 78 is generally coaxial, and a proximal anchor 84 (e.g., second anchor) with an initial engagement being generally perpendicular with the suture 78.

As stated above, an introducer sheath (not shown) can first be placed within a patient's urethra for the purpose of facilitating access to a treatment site. The distal anchor 70 is "unsheathed" from the needle delivery mechanism once positioned for reliable deployment eliminating predicate distal suture. This results in an adjustable implant length. This distal anchor 70 configuration also provides increased yield and strength.

With reference now to FIGS. 11A-F, in one particular, non-limiting use in treating a prostate, an elongate tissue access portion 404 of a delivery device 400 is placed within a urethra (UT) leading to a urinary bladder (UB) of a patient. The delivery device can be placed within an introducer sheath previously positioned in the urethra or alternatively, the delivery device can be inserted directly within the urethra. The patient is positioned in lithotomy. The elongate portion 404 is advanced within the patient until a leading end 410 thereof reaches a prostate gland (PG). In a specific approach, the side(s) (i.e., lobe(s)) of the prostate to be treated is chosen while the device extends through the bladder and the device is turned accordingly. The device is first positioned at the bladder neck and then retracted approximately 1 cm while keeping the device parallel to the prostatic fossa and preserving mucosa. The distal end of the elongate portion can be used to push the urethra into the prostate gland. The inside of the prostate gland (i.e., adenoma) is spongy and compressible and the outer surface (i.e., capsule) of the prostate gland is firm. By the physician viewing with the endoscope, he/she can push the urethra into the prostate gland compressing the adenoma and creating the desired opening through the urethra. To accomplish this, the physician pivots the tool laterally about the pubic symphysis, generally about 20 to 30 degrees (See FIG. 11A). The physician then rotates the tool anterior between 9 and 10 o'clock for the patient's side right lobe and between 2 and 3 o'clock for the patient's side left lobe. Viewing through the endoscope, the physician wants to have about the same amount of tissue protruding on both sides of the elongate shaft (See FIG. 11B).

Figure 11A:
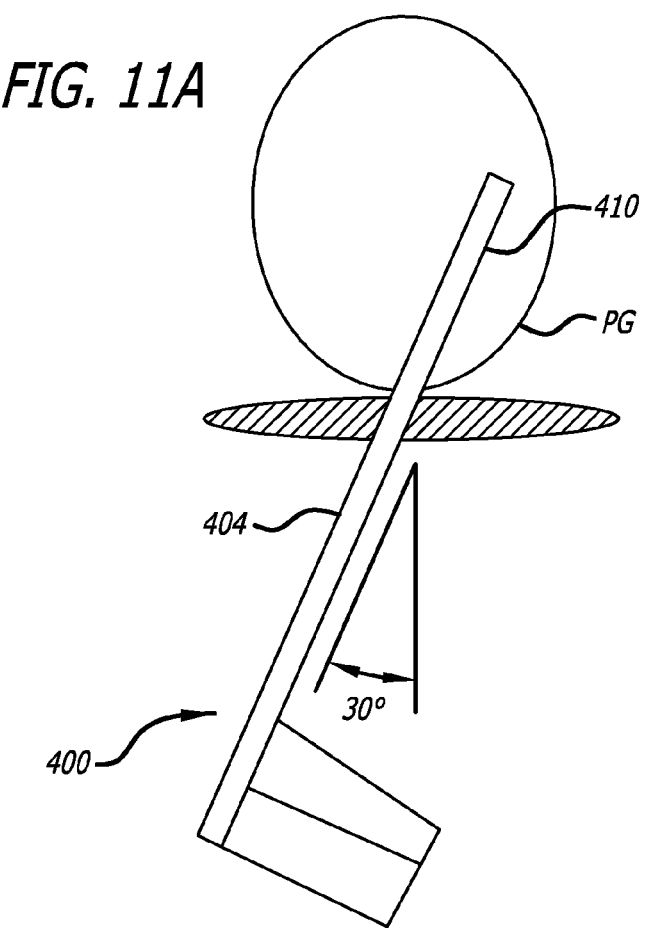
FIGS. 11A-F are partial views of a coiled anchor assembly being implanted through the prostate of an individual with benign prostatic hyperplasia.
Figure 11B:
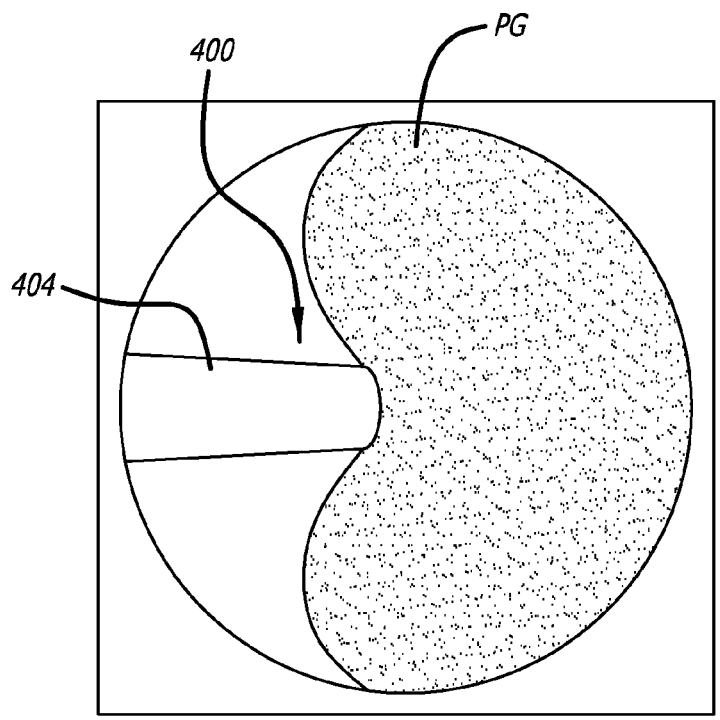
Figure 11C:
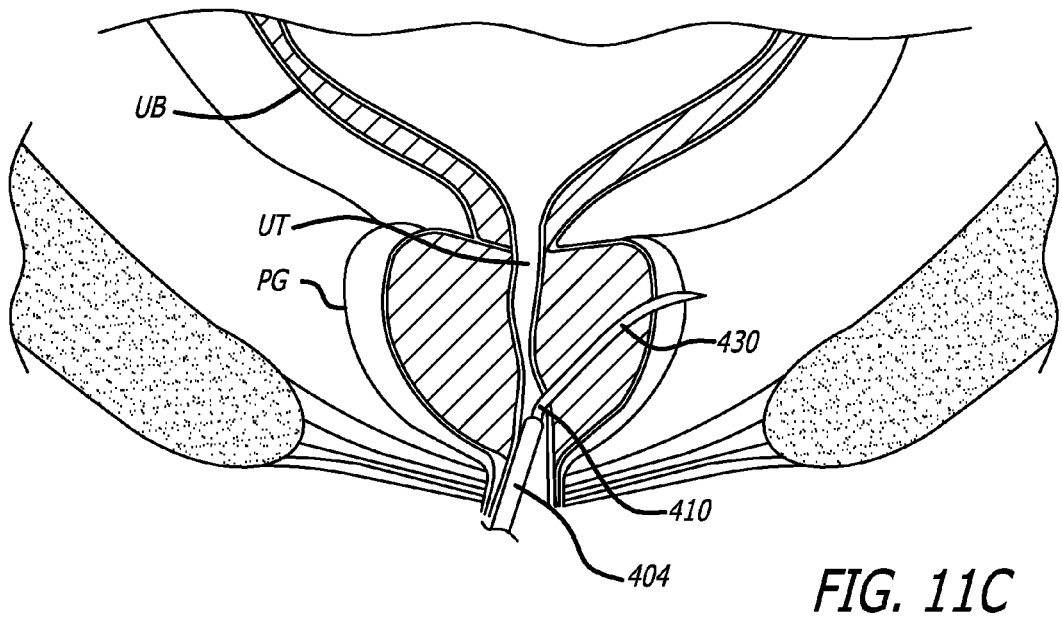
Figure 11D:
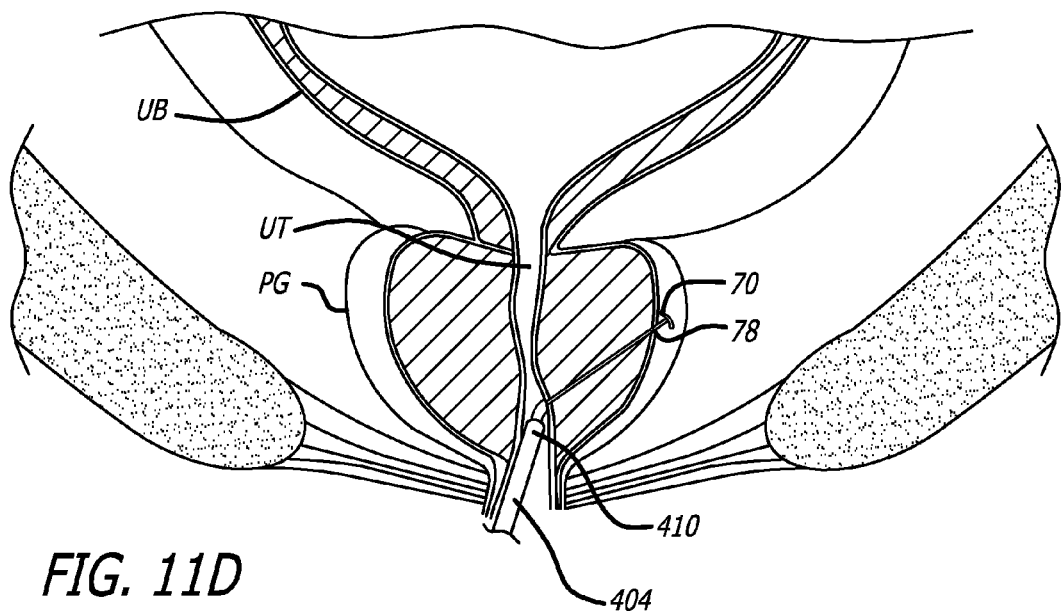

At the leading end 410 of the delivery device, as shown in FIG. 11C, a needle 430 carrying an anchor assembly is ejected into and through tissue. The needle assembly can be configured so that it curves back toward the delivery tool as it is ejected. In use in a prostate intervention, the needle assembly 430 is advanced through and beyond a prostate gland (PG). The delivery device can be rotated anteriorly to lift a prostatic lobe.

Figure 11E:
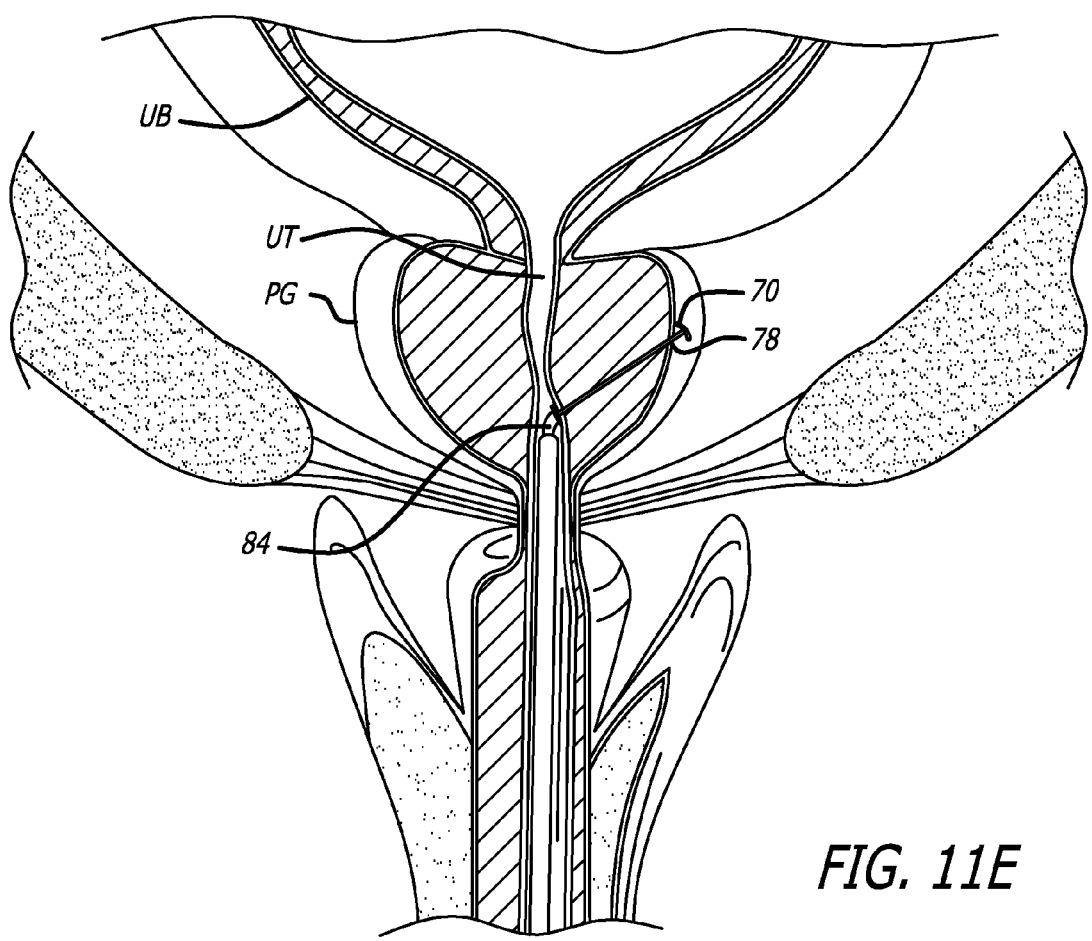

Upon withdrawal of the needle assembly 430 (See FIG. 11D), the distal anchor 20 is left beyond the prostate (PG). Next, steps are taken to implant the proximal anchor 84 within the urethra (FIG. 11E). Either a single anchor assembly or multiple anchor assemblies can be delivered and deployed at an intervention site by the deployment device (See FIG. 11F). Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

The disclosed embodiments contemplate both pushing directly on anchor portions of an anchor assembly as well as pushing directly upon the connector of the anchor assembly. Further, an anchor assembly can be delivered and deployed at an interventional site by a deployment device. Consequently, in the context of prostate treatment, the disclosed embodiments accomplish both compressing of the prostate gland and the opening of the prostatic urethra and applying tension between ends of the implant. Moreover, drug delivery is contemplated as a further remedy in BPH and over-active bladder treatment.

Once implanted, the anchor assembly of the disclosed embodiments accomplishes desired tissue approximation, manipulation, compression or retraction, as well as cooperates with the target anatomy to provide an atraumatic support structure. In particular, the shape and contour of the anchor assembly can be configured so that the assembly invaginates within target tissue, such as within natural folds formed in the urethra by the opening of the urethra lumen by the anchor assembly. In fact, in situations where the anchor assembly is properly placed, wispy or pillowy tissue in the area collapses around the anchor structure. Eventually, the natural tissue can grow over the anchor assembly, and new cell growth occurs over time. Such cooperation with target tissue facilitates healing and avoids unwanted side effects such as calcification or infection at the interventional site.

Furthermore, in addition to an intention to cooperate with natural tissue anatomy, the disclosed embodiments also contemplate approaches to accelerate healing or induce scarring. Manners in which healing can be promoted can include employing abrasive materials, textured connectors, biologics and drugs.

Figure 11F:
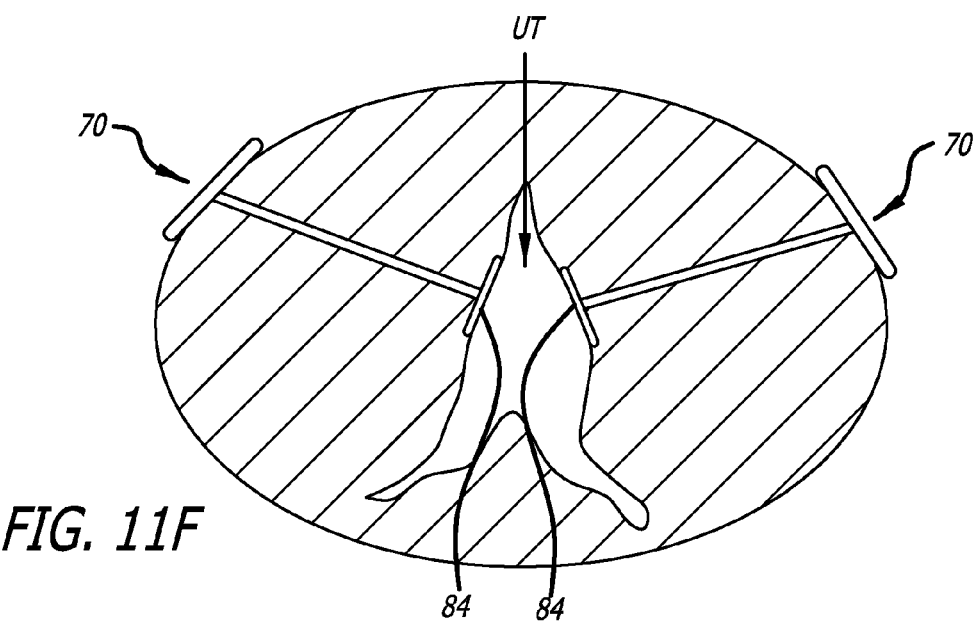

It has been observed that placing the anchors at various desired positions within the anatomy can extract the best results. For example, when treating a prostate, one portion of an anchor can be placed within a urethra. It has been found that configuring such anchors so that ten o'clock and two o'clock positions (when looking along the axis of the urethra) are supported or retained, effectively holds the anatomy open and also can facilitate invagination of the anchor portion within natural tissue. Typically, one to two pairs of anchor assemblies are implanted to create an anterior channel along the urethra within the prostate gland (FIG. 11F). This is particularly true in the regions of anatomy near the bladder and the juncture at which the ejaculatory duct connects to the urethra.

Moreover, it is to be recognized that the foregoing procedure is reversible. In one approach, the connection of an anchor assembly can be severed and a proximal (or second) anchor component removed from the patient's body. For example, the physician can simply cut the connector and simultaneously remove the second anchor previously implanted for example, in the patient's urethra. It is to be recognized that various materials are contemplated for manufacturing the disclosed devices. Moreover, one or more components such as distal anchor, proximal anchor, suture, of the one or more anchor assemblies disclosed herein may be designed to be completely or partially biodegradable or biofragmentable.

Further, as stated, the systems and methods disclosed herein may be used to treat a variety of pathologies in a variety of tubular structures comprising a cavity or a wall. Examples of such organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, and the like.

Finally, it is to be appreciated that the invention has been described hereabove with reference to certain examples or embodiments, but that various additions, deletions, alterations and modifications may be made to those examples and embodiments without departing from the intended spirit and scope of the disclosed embodiments. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

The various embodiments described above are provided by way of illustration only and should not be construed to limit the disclosed embodiments. Those skilled in the art will readily recognize various modifications and changes that may be made to the disclosed embodiments without following the example embodiments and applications illustrated and described herein, and without departing from the true spirit and scope of the disclosed embodiments, which is set forth in the following claims.

What is claimed is:

1. A system for delivering an anchor assembly for applying retractive pressure to tissue, comprising:
   a distal anchor, wherein the distal anchor includes a head portion that is connected to a generally perpendicularly oriented tail portion via a connecting mid-section portion;
   a suture, wherein the suture is attachable and tensioned to the distal anchor; and
   a coiled proximal anchor for securing the suture as part of a proximal end of the anchor assembly, the coiled proximal anchor including a body, a portion of which includes coils with varying pitch, and a plug sized to be received within an internal bore of the body.

2. The system of claim 1, wherein the varying pitch extends from a first end of the body to a midsection of the body.

3. The system of claim 1, wherein the varying pitch extends a full length of the body.

4. The system of claim 1, further comprising a delivery apparatus, the delivery apparatus including a slot for registering the coiled proximal anchor.

5. The system of claim 4, the delivery apparatus including means for rotating the coiled proximal anchor onto the suture.

6. The system of claim 1, wherein the body includes coils spaced to grasp and bite into the suture.

7. The system of claim 6, wherein the coils are formed from a flat wire having edges that bite into the suture.

8. The system of claim 1, wherein the proximal anchor is formed from a bifilar winding of two wires.

9. The system of claim 8, wherein the varying pitch is created by the bifilar winding.

10. The system of claim 1, the proximal anchor further comprising a tubular portion connected to a coil portion.

11. The system of claim 10, wherein the coil portion is intended to assume both longitudinally extended and contracted configurations.

12. The system of claim 11, wherein the coiled portion grasps the suture when in the contracted configuration.

13. The system of claim 1, wherein the delivery apparatus includes means for translating the plug within the internal bore.

14. The system of claim 1, the plug further comprising a slot for receiving and engaging the suture.

15. The system of claim 1, wherein the distal anchor includes a distal coil portion connected to the tail portion.

16. A system for delivering an anchor assembly for applying retractive pressure to tissue, comprising:
    a distal anchor, wherein the distal anchor includes a head portion that is connected to a generally perpendicularly oriented tail portion via a connecting mid-section portion;
    a suture, wherein the suture is attachable and tensioned to the distal anchor; and
    a coiled proximal anchor for securing the suture as part of a proximal end of the anchor assembly, the coiled proximal anchor including a body, a portion of which includes coils with varying pitch, and the proximal anchor further comprising an H-shaped substructure configured to receive the body of the coiled proximal anchor.

17. The system of claim 16, wherein the varying pitch extends from a first end of the body to a midsection of the body.

18. The system of claim 16, wherein the varying pitch extends a full length of the body.

19. The system of claim 16, further comprising a delivery apparatus, the delivery apparatus including a slot for registering the coiled proximal anchor.

20. The system of claim 19, the delivery apparatus including means for rotating the coiled proximal anchor onto the suture.

21. The system of claim 16, wherein the body includes coils spaced to grasp and bite into the suture.

22. The system of claim 21, wherein the coils are formed from a flat wire having edges that bite into the suture.

23. The system of claim 16, wherein the coiled proximal anchor is formed from a bifilar winding of two wires.

24. The system of claim 23, wherein the varying pitch is created by the bifilar winding.

25. The system of claim 16, the coiled proximal anchor further comprising a tubular portion connected to a coil portion.

26. The system of claim 25, wherein the coil portion is intended to assume both longitudinally extended and contracted configurations.

27. The system of claim 26, wherein the coiled portion grasps the suture when in the contracted configuration.

28. The system of claim 16, wherein the H-shaped substructure includes a first arm sized to receive a first coil and a second arm sized to receive a second coil.

29. The system of claim 16, wherein the distal anchor includes a distal coil portion connected to the tail portion.

* * * * *